United States Patent [19]

Garris

[11] Patent Number: 5,541,150
[45] Date of Patent: Jul. 30, 1996

[54] SEQUESTERED COPPER ALGICIDES USING IONIC POLYMERIC STABILIZING AGENTS

[75] Inventor: John P. Garris, Cumming, Ga.

[73] Assignee: BioLab, Inc., Decatur, Ga.

[21] Appl. No.: 486,832

[22] Filed: Jun. 7, 1995

[51] Int. Cl.$^6$ .............................. A01N 59/20; A01N 55/02
[52] U.S. Cl. ........................... 504/152; 504/151; 504/157
[58] Field of Search ..................................... 504/151, 152, 504/157

[56] References Cited

U.S. PATENT DOCUMENTS

| | | | |
|---|---|---|---|
| 2,734,028 | 2/1956 | Domogalla | 504/152 |
| 3,798,248 | 3/1974 | van Koten et al. | 556/22 |
| 3,821,369 | 6/1974 | Brink, Jr. et al. | 424/141 |
| 3,930,834 | 1/1976 | Schulteis et al. | 71/67 |
| 4,324,578 | 4/1982 | Seymour et al. | 71/67 |
| 5,149,354 | 9/1992 | Delaney | 514/495 |
| 5,160,527 | 11/1992 | Law et al. | 514/372 |

OTHER PUBLICATIONS

"Citric Acid Enhancement of Copper Solubility and Toxicity in Bicarbonate Solutions" by J. A. Swader and Wing–Yee Chan, Pesticide Biochemistry and Physiology 5, 405–411 (1975).

"Guidelines for Applying Copper Sulfate as an Algicide: Lake Loami Field Study," Illinois State Water Survey, Peoria, Illinois, U.S. Department of Commerce, National Technical Information Service, Oct. 1988.

*Primary Examiner*—Richard L. Raymond
*Assistant Examiner*—Brian Bembenick
*Attorney, Agent, or Firm*—Woodard, Emhardt, Naughton Moriarty & McNett

[57] ABSTRACT

Copper-containing algicides for treating swimming pool water without staining are disclosed. The algicidal compositions include a source of copper and a polymeric sequestering agent. The polymeric sequestering agent may be a water-soluble anionic or cationic polymer. Conventional sequestering agents may also be included in the composition.

26 Claims, 3 Drawing Sheets

SEQUESTERED COPPER ALGICIDES USING IONIC POLYMERIC STABILIZING AGENTS

FIELD OF THE INVENTION

The present invention relates generally to algicides for water systems such as swimming pools, and more particularly to algicides using copper as their active agent.

BACKGROUND OF THE INVENTION

Water soluble elemental copper, such as copper sulfate, is known to possess algicidal qualities when used in circulating water systems. Unfortunately, copper ions easily precipitate in alkaline or near-alkaline water conditions as insoluble salts of oxides, hydroxides, and/or carbonates, removing the copper from the system and thus removing the ability of the copper ion to act as an algicide.

In order to improve the efficacy of copper as an algicide, sequestering agents, such as alkanolamines, aminocarboxylic acids or citric acid have been used to improve the stability of copper in these conditions. These simple, organic compounds contain amine, hydroxyl, and carboxyl functionalities that exhibit sequestration capacity for polyvalent cations. Problems remain however, because alkanolamines, aminocarboxylic acids, and citric acid deteriorate quickly in the presence of halogens and other oxidizers, bacteria, sunlight or heat, thus allowing the copper to become unsequestered and subject to loss due to precipitation.

Another problem encountered in water treatment applications, such as swimming pools, is that copper precipitates to form unsightly stains on the pool's surface. In particular, copper hydroxides, copper oxides and copper carbonates are known to cause unsightly stains that are difficult to remove.

A need therefore exists for a method of stabilizing soluble copper for longer periods of time during treatment and application, thereby increasing its effective life and preventing stains from occurring on swimming pool surfaces. The present invention addresses that need.

SUMMARY OF THE INVENTION

Briefly describing one aspect of the present invention there is provided copper-containing algicides for treating swimming pool water without staining the sides of the pool. The inventive algicidal compositions include a source of copper and a polymeric sequestering agent, which polymeric sequestering agent may be a water-soluble anionic polymer or a water-soluble cationic polymer. Conventional sequestering agents may also be included in the composition.

One object of the present invention is to provide copper-containing algicides that do not stain the solid surfaces of a swimming pool.

Further objects and advantages of the present invention will be apparent from the following description.

DESCRIPTION OF THE PREFERRED EMBODIMENT

Figure 1:
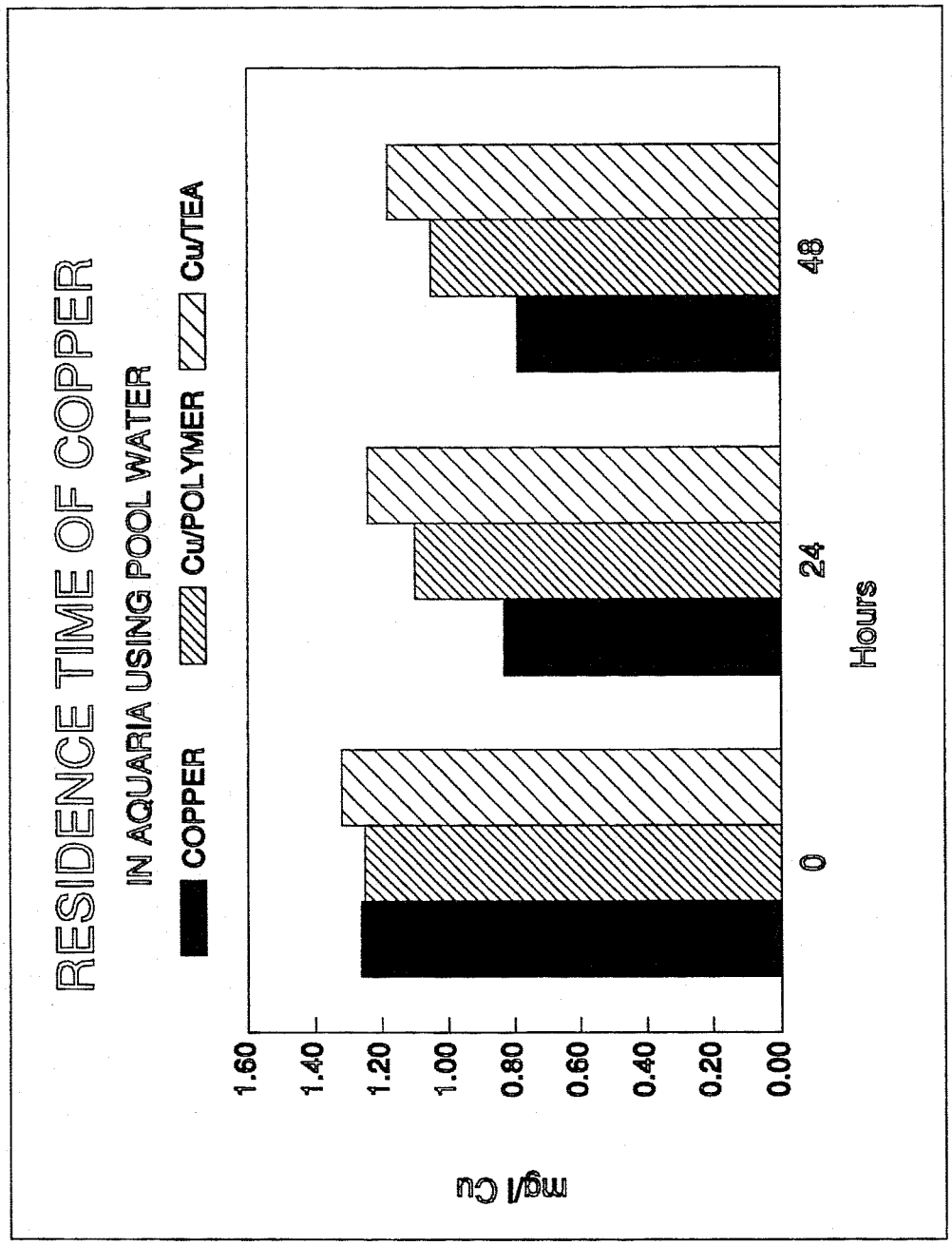
FIG. 1 shows the residence time of soluble copper, copper/polymer and copper triethanolamine using 28 liter aquaria (error bars equal to ± one std. deviation).

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the described device, and such further applications of the principles of the invention as illustrated therein being contemplated as would normally occur to one skilled in the art to which the invention relates.

As previously indicated, the invention relates to an improved algicidal formulation for water treatment applications based on an improved method of stabilizing copper. The invention employs ionic polymeric stabilizing agents, preferably in conjunction with a conventional organic sequestering agent such as alpha-hydroxyacids and the like, to sequester elemental copper. This formulation stabilizes copper even in alkaline environments and prevents its loss due to precipitation, thereby increasing the effective life of the algicide and preventing staining of swimming pool surfaces.

In one aspect of the present invention the copper is provided as copper sulfate or as soluble or insoluble copper salts such as copper acetate, copper chloride, copper formate and copper carbonate.

In some preferred embodiments, the invention uses water-soluble anionic polymers such as polyacrylic acid, polymethacrylic acid, polyvinyl sulfonic acid, polystyrene sulfonic acid, polymaleic acid, polyaspartic acid, copolymers, terpolymers, or tetrapolymers thereof or the sodium, potassium, or calcium salts of said polymers. In other preferred embodiments, water-soluble cationic polymers such as poly [oxyethylene-(dimethylimino) ethylene-(dimethylimino) ethylene dichloride], polyvinyl amine, chitosan, polyethylene amine or a polymer of 1,6-hexanediamine-N,N,N',N'-tetramethyl or the fluoride, chloride, or bromide salts thereof, and the like are used.

As to the relative amounts of the various components, preferably about 0.1 to about 5.0 moles of polymer are added to the formulation for each mole of copper, with 1.0 to 3.0 moles polymer to each mole of copper being preferred.

The molecular weight of the ionic polymeric agent is preferably between about 500 Da to 100,000 Da, with polymers having a molecular weight of between about 1,000 Da and 20,000 Da being most preferred.

In one aspect of the invention, conventional organic sequestering agents are used with the polymeric agent. For example, hydroxy-carboxylic acids, aminocarboxylic acids, polyamines, alkanolamines, polyphosphates, phosphonic acids, crown ethers, amino acids, etc. may be used in conjunction with the polymeric agent as described below. In certain preferred embodiments organic acids such as, e.g., oxalic acid, suberic acid, acetic acid, tricarballic acid, succinic acid, malonic acid and maleic acid, and the salts thereof, are used. Especially preferred are the hydroxy-carboxylic acids such as, e.g., citric acid, gluconic acid, tartronic acid, lactic acid, tartaric acid, malic acid, glyceric acid, or tetrahydroxy succinic acid, and the salts thereof, and the lactone forms of such acids. The organic acids and hydroxy-acids are preferred in certain embodiments because the other noted sequestering agents are sources of nitrogen and phosphorous, two critical nutrients for algae growth.

A ratio of 0.1 to 5.0 moles of conventional sequestering agent is typically added for each mole of copper in the formulation, with 0.5 to 2.0 moles of sequestering agent to each mole of copper being preferred. The amount of elemental copper sequestered in the formulation may range from 0 to 15%, with 1 to 10% being preferred, and 3 to 8% being most preferred.

EXAMPLE 1

Preparation of composition with an anionic polymer

Forty grams of a 50% solution of partially neutralized (10 to 50 percent) polyacrylic acid was combined with 25 grams of anhydrous citric acid, 15 grams of water and 20 grams of copper sulfate pentahydrate. This formulation was heated and stirred to allow the copper sulfate to go into solution. This formulation yields a thick royal blue liquid that contains 5.1% elemental copper.

EXAMPLE 2

Preparation of composition with an anionic polymer and a conventional organic sequestering agent Forty grams of a 50% solution of a copolymer of maleic anhydride and styrene sulfonate, 20 grams of gluconodeltalactone and 22 grams of copper acetate are heated and stirred with 18 grams of water to yield a very dark blue liquid formulation that contains 7.8% elemental copper.

EXAMPLE 3

Preparation of a composition with a water-soluble cationic polymer

Thirty-five grams of ethylene-diamine tetraacetic acid disodium salt (EDTA) is reacted with 13.5 grams of copper carbonate and 41.5 grams water. Some carbon dioxide is released in this reaction. 30 grams of a 50% solution of a polymer of 1,6-hexanediamine-N,N,N',N'-tetramethyl chloride salt is added. This formulation will yield a thick blue liquid that contains 5.8% elemental copper.

EXAMPLE 4

Preparation of composition with an anionic polymer and a conventional organic sequestering agent Forty grams of a 40% solution of 2-Propenoic acid polymer with 2-hydroxy-3-(2-propenyloxy)-1-propanesulfonic acid monosodium salt (a copolymer of acrylic acid and an allyloxy, hydroxypropyl sulfonate), 20 grams of gluconodeltalactone and 28 grams of copper sulfate pentahydrate are heated and stirred with 8 grams of potassium hydroxide and 4 grams of water to yield a very dark blue liquid formulation that contains 7.1% elemental copper.

EXAMPLE 5

Preparation of composition with an anionic polymer

Fifty grams of a 40% solution of 2-Propenoic acid polymer with 2-hydroxy-3-(2-propenyloxy)-1-propanesulfonic acid monosodium salt (a copolymer of acrylic acid and an allyloxy, hydroxypropyl sulfonate), 12 grams of hydrochloric acid and 25 grams of copper sulfate pentahydrate are heated and stirred with 13 grams of water to yield a very dark blue liquid formulation that contains 6.4% elemental copper.

EXAMPLES 6–8

Algicidal Effectiveness

Minimum inhibitory concentration (MIC) laboratory studies were performed to demonstrate that the compositions of the present invention retained their algicidal efficacy. MIC data gives the minimum concentration of algicide needed to prevent growth of the algae in a culture.

The MIC studies are performed in sterile glassware using both viability and sterility controls. An algae suspension is added to test tubes containing the appropriate amounts of test biocide and the tubes are incubated for two weeks under fluorescent lights (on a "12 hour on"/"12 hour off" lighting regimen). The cultures are then measured by visual observation to determine the presence of living algae. As seen in Tables 1–3, there was equivalent algicidal activity between free elemental copper as copper sulfate, copper complexed with triethanolamine ("TEA"), and the polymer sequestered copper at equivalent doses of active copper present against various blue-green and green algal species.

TABLE 1

| MIC results against Phormidium sp. using various concentrations of copper. | | | | | |
|---|---|---|---|---|---|
| Copper Conc. (ppm) | 0.50 | 0.25 | 0.125 | 0.065 | 0.025 |
| Unsequestered Copper | – | – | – | – | – |
| TEA Sequestered Copper | – | – | – | – | – |
| Polymer Sequestered Copper | – | – | – | – | – |

(–) indicates no algae growth was seen
(+) indicates algae growth was seen

TABLE 2

| MIC results against Phormidium inudatum using various concentrations of copper. | | | | | |
|---|---|---|---|---|---|
| Copper Conc. (ppm) | 3.0 | 1.0 | 0.5 | 0.25 | 0.125 |
| Unsequestered Copper | – | – | – | – | – |
| TEA Sequestered Copper | – | – | – | – | – |
| Polymer Sequestered Copper | – | – | – | – | – |

(–) indicates no algae growth was seen
(+) indicates algae growth was seen

TABLE 3

| MIC results against Chlorella sp. using various concentrations of copper. | | | | | |
|---|---|---|---|---|---|
| Copper Conc. (ppm) | 10.0 | 9.0 | 8.0 | 7.0 | 6.0 |
| Unsequestered Copper | – | – | – | – | – |
| TEA Sequestered Copper | – | – | – | – | – |
| Polymer Sequestered Copper | – | – | – | – | + |

(–) indicates no algae growth was seen
(+) indicates algae growth was seen

EXAMPLE 10

Field Tests

Further tests were done using test swimming pools infested with algae. These pools were treated with either the polymer sequestered copper or copper triethanolamine at a concentration of 0.7 to 0.5 ppm. All the pools treated with the formulation of the invention killed the algae; however some of those pools treated with the copper triethanolamine complex failed to kill the algae. The polymer additive may, unexpectedly, effectively "deliver" the copper to the cell wall, thus bringing higher concentrations of the copper in closer contact with the cell. This may be a mechanism to explain the result because copper triethanolamine works by simple diffusion.

EXAMPLE 11

Residence Time of Copper

Soluble elemental copper is easily removed from solution through filtration and by combining with carbonate and hydroxide ions that are commonly found in process water, such as swimming pools, to form insoluble copper carbonates and hydroxides. Sequestered copper does not readily form these insoluble salts or filter out of the system. Thus, sequestered copper has a higher residence time in the pool. This allows the copper to work for longer periods of time.

The residence time of copper was tested using a system of aquaria. Copper was tested in various sequestered forms and as free soluble copper. Initially, the copper concentration will be 1.25 ppm as $Cu^{++}$. Copper concentrations were tested photometrically using a HACH 3000 colorimeter.

Initial copper concentrations were tested 15 minutes after the addition of granular or liquid ingredients. Copper concentrations were checked at 24 hours and 48 hours. The volume of the aquarium is 28 liters. The experimental design tested a copper sulfate only control, a copper triethanolamine (TEA) complex, and the polymer-copper.

EXAMPLE 12

Residence Time in Field Tests

Figure 2:
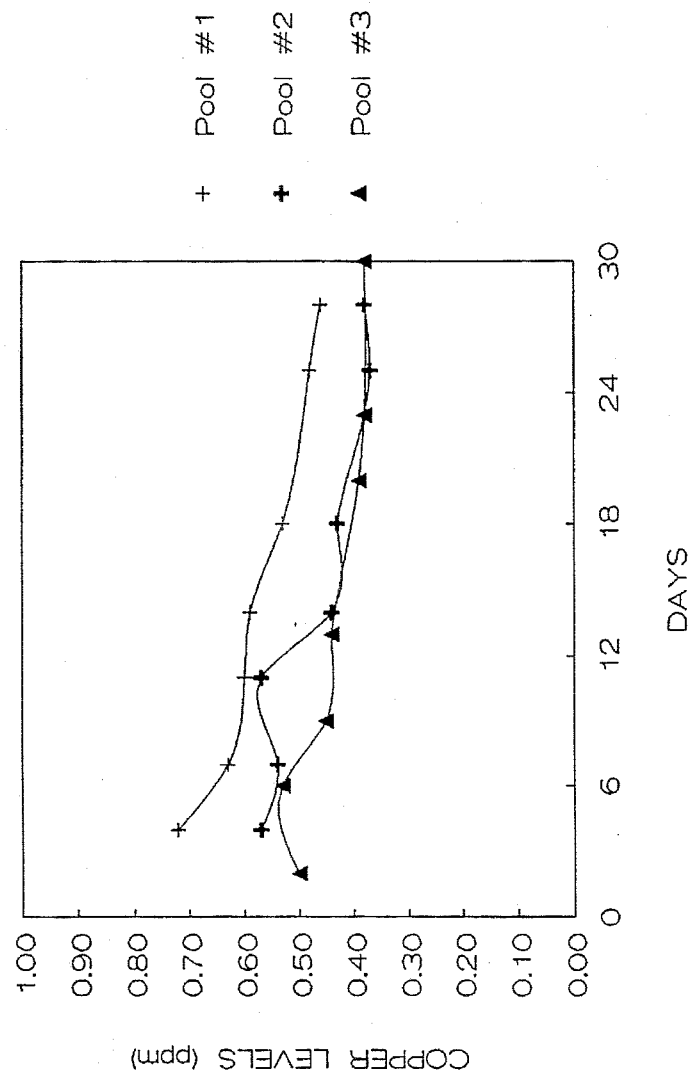
FIGS. 2 and 3 show equivalent residence times for those samples containing copper/TEA and copper/polymer formulations.
Figure 3:
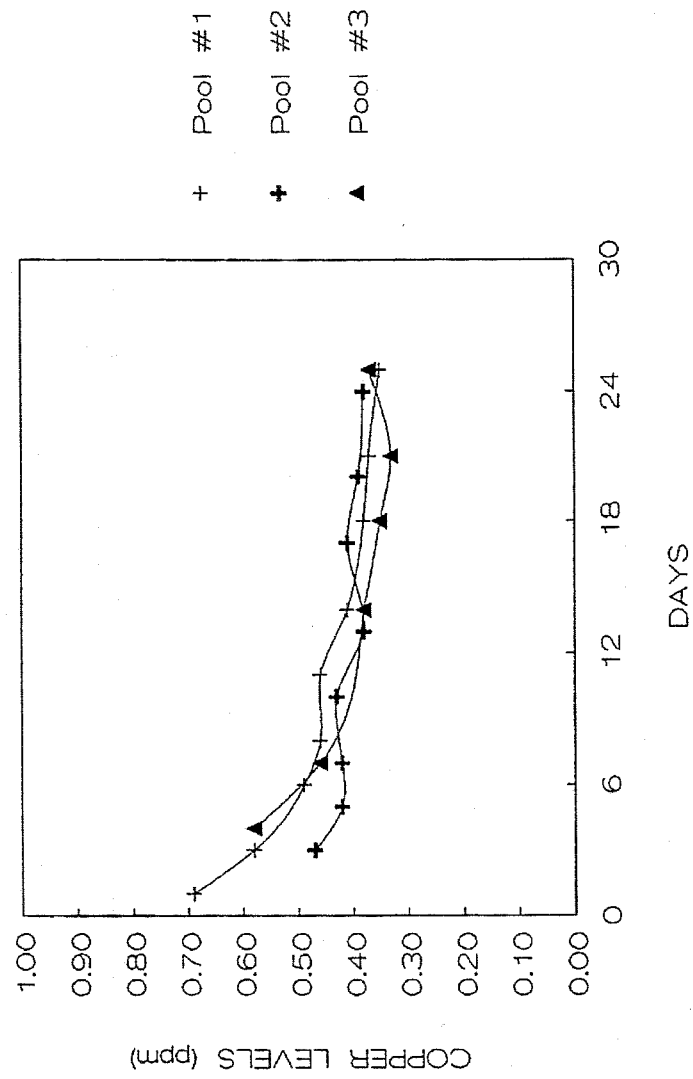

Residence times were tracked in field pools that were treated with either copper sequestered with TEA or copper sequestered with polymer. The tests show equivalent residence times for those samples containing copper/TEA and copper/polymer formulations. See FIGS. 2 & 3.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An algicidal composition for treating water, comprising:
   (a) an algicidally effective source of copper; and
   (b) a water-soluble anionic or cationic polymeric sequestering agent with a molecular weight between about 500 Da and about 100,000 Da.

2. An algicidal composition according to claim 1 wherein said polymeric sequestering agent is a water-soluble anionic polymer.

3. An algicidal composition according to claim 1 wherein said polymeric sequestering agent is a water-soluble cationic polymer.

4. An algicidal composition according to claim 1 and further including an organic sequestering agent differing in composition from said polymeric sequestering agent.

5. An algicidal composition according to claim 2 wherein said water-soluble anionic polymer is a member selected from the group consisting of polyacrylic acid, polymethacrylic acid, polyvinyl sulfonic acid, polystyrene sulfonic acid, polymaleic acid, and polyaspartic acid.

6. An algicidal composition according to claim 5 wherein said water-soluble anionic polymer is a copolymer, terpolymer, or tetrapolymer of one or more of said water-soluble anionic polymers.

7. An algicidal composition according to claim 5 wherein said water-soluble anionic polymer is provided as a salt.

8. An algicidal composition according to claim 3 wherein said water-soluble cationic polymer is a member selected from the group consisting of poly[oxyethylene-(dimethylimino) ethylene-(dimethylimino) ethylene dichloride], polyvinyl amine, chitosan, polyethylene amine, polymers of 1,6-hexanediamine-N,N,N'-tetramethyl.

9. An algicidal composition according to claim 8 wherein said water-soluble cationic polymer is provided as a salt.

10. A method of reducing the ability of copper-containing algicides to stain pool surfaces, comprising providing the copper-containing algicide to a pool in a form in which at least some of the copper is sequestered by a water-soluble anionic or cationic polymeric sequestering agent with a molecular weight between about 500 Da and about 100,000 Da.

11. A method according to claim 10 wherein said polymeric sequestering agent is a water-soluble anionic polymer.

12. A method according to claim 10 wherein said polymeric sequestering agent is a water-soluble cationic polymer.

13. A method according to claim 10 wherein said algicidal composition further includes an organic sequestering agent differing in composition from said polymeric sequestering agent.

14. A method according to claim 10 wherein said water-soluble anionic polymer is a member selected from the group consisting of polyacrylic acid, polymethacrylic acid, polyvinyl sulfonic acid, polystyrene sulfonic acid, polymaleic acid, and polyaspartic acid.

15. A method according to claim 11 wherein said water-soluble anionic polymer is a copolymer, terpolymer, or tetrapolymer of one or more of said water-soluble anionic polymers.

16. A method according to claim 11 wherein said water-soluble anionic polymer is provided as a salt.

17. A method according to claim 12 wherein said water-soluble cationic polymer is a member selected from the group consisting of poly[oxyethylene-(dimethylimino) ethylene-(dimethylimino) ethylene dichloride], polyvinyl amine, chitosan, polyethylene amine, polymers of 1,6-hexanediamine-N,N,N',N'-tetramethyl.

18. A method according to claim 12 wherein said water-soluble cationic polymer is provided as a salt.

19. A method extending the useful life of a copper-containing algicide, comprising providing the copper-containing algicide to a pool in a form in which at least some of the copper is sequestered by a water-soluble anionic or cationic polymeric sequestering agent with a molecular weight between about 500 Da and about 100,000 Da.

20. A method according to claim 19 wherein said polymeric sequestering agent is a water-soluble anionic polymer.

21. A method according to claim 19 wherein said polymeric sequestering agent is a water-soluble cationic polymer.

22. A method according to claim 19 wherein said algicidal composition further includes an organic sequestering agent differing in composition from said polymeric sequestering agent.

23. A composition, comprising copper bound to a water-soluble anionic or cationic polymeric sequestering agent with a molecular weight between about 500 Da and about 100,000 Da.

24. A composition according to claim 23 wherein said polymeric sequestering agent is present in the amount of about 0.1 to 5.0 moles of polymeric sequestering agent to each mole of copper.

25. A composition according to claim 24 wherein said polymeric sequestering agent is present in the amount of about 1.0 to 3.0 moles of polymeric sequestering agent to each mole of copper.

26. A composition according to claim 23 wherein said polymeric sequestering agent has a molecular weight of between about 1,000 Da and about 20,000 Da.

* * * * *